(12) United States Patent  (10) Patent No.: US 7,747,303 B2
Eichler  (45) Date of Patent: Jun. 29, 2010

(54) ELECTRODE SYSTEM

(76) Inventor: Ruediger Eichler, Tiefenbacherstrasse 5, 97225 Zellingen (DE)

( * ) Notice: Subject to any disclaimer, the term of this patent is extended or adjusted under 35 U.S.C. 154(b) by 1291 days.

(21) Appl. No.: 10/525,053

(22) PCT Filed: Nov. 26, 2002

(86) PCT No.: PCT/EP02/13327

§ 371 (c)(1),
(2), (4) Date: Aug. 3, 2005

(87) PCT Pub. No.: WO2004/021880

PCT Pub. Date: Mar. 18, 2004

(65) Prior Publication Data

US 2006/0058600 A1 Mar. 16, 2006

(30) Foreign Application Priority Data

Aug. 21, 2002 (DE) .............................. 102 38 310

(51) Int. Cl.
A61B 5/0488 (2006.01)
(52) U.S. Cl. ...................................... 600/390; 600/393
(58) Field of Classification Search ................. 600/390, 600/393, 506, 547
See application file for complete search history.

(56) References Cited

U.S. PATENT DOCUMENTS 4,026,278 A 5/1977 Ricketts et al.
4,763,660 A * 8/1988 Kroll et al. ................... 600/391
5,313,952 A 5/1994 Hoch
5,341,806 A * 8/1994 Gadsby et al. ............... 600/393
6,205,346 B1 3/2001 Akiva
6,272,365 B1 8/2001 Ronkainen et al.
6,400,975 B1 * 6/2002 McFee ........................ 600/372

FOREIGN PATENT DOCUMENTS

| DE | 34 86 127 T2 | 7/1993 |
| DE | 42 25 958 A1 | 12/1993 |
| EP | 0 509 689 B1 | 10/1992 |
| WO | WO 02/053028 A2 | 7/2002 |

* cited by examiner

Primary Examiner—Lee S Cohen
(74) Attorney, Agent, or Firm—Gallagher & Kennedy PA; Thomas MacBlain; Andrea Nicholson

(57) ABSTRACT

This invention relates to an electrode arrangement (1), in particular for electroimpedance tomography, having multiple electrodes (4) for electric contacting of measurement object and a belt-shaped electrode carrier (3.1-3.4) for encompassing the measurement object, with the electrodes (4) being attached to the belt-shaped electrode carrier (3.1-3.4). It is proposed that the electrodes (4) be positionable on the belt-shaped electrode carrier (3.1-3.4) in the longitudinal direction of the belt-shaped electrode carrier (3.1-3.4). In addition, this invention relates to a method for applying such an electrode arrangement to a measurement object.

27 Claims, 4 Drawing Sheets

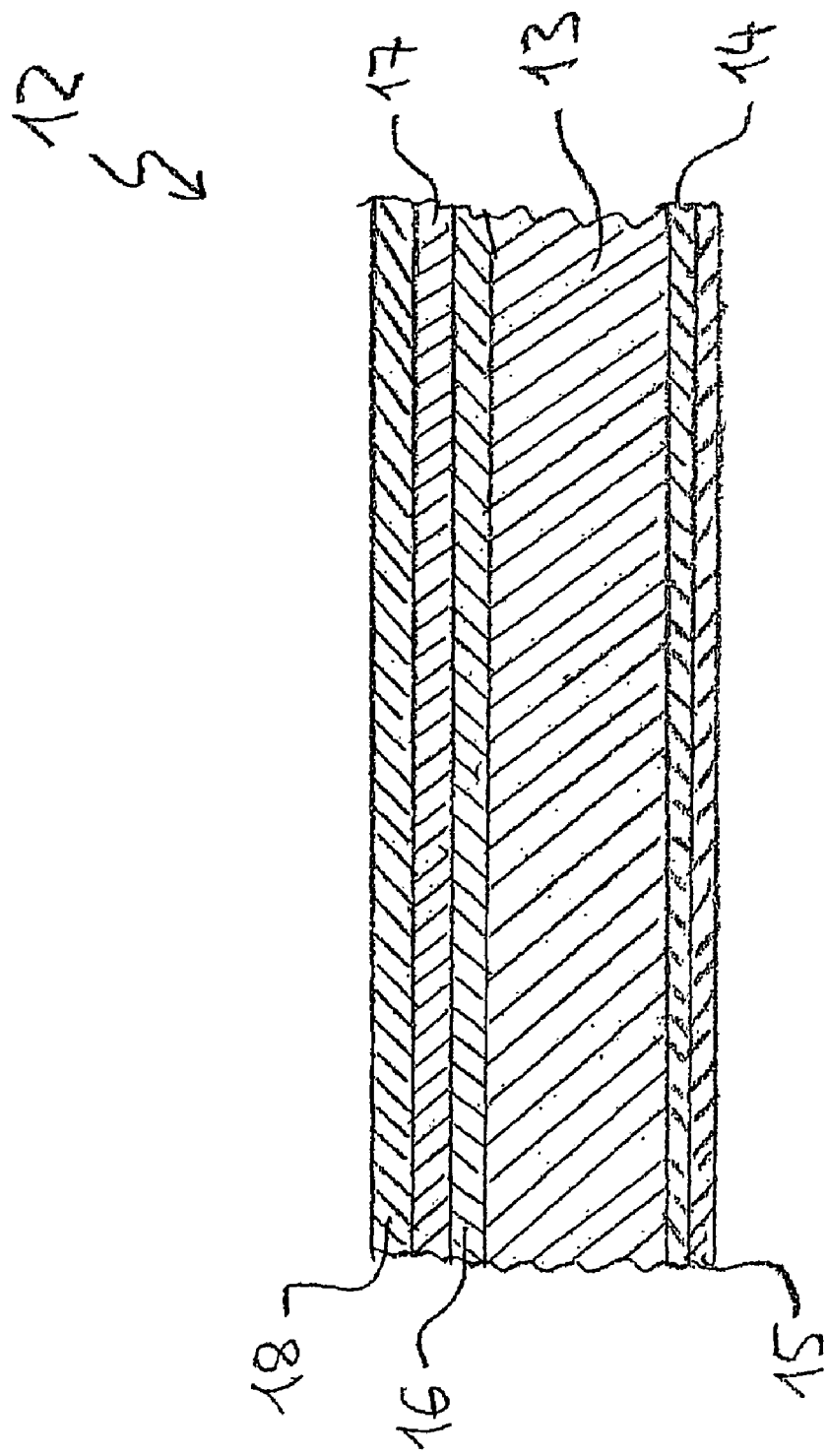

ELECTRODE SYSTEM

FIELD OF THE INVENTION

This invention relates to an electrode arrangement, in particular for electroimpedance tomography and a method for applying such an electrode arrangement to a measurement object.

BACKGROUND OF THE INVENTION

To perform so-called electroimpedance tomography on a patient, several electrodes must be attached to the patient's chest, where accurate positioning of the electrodes and constant contact with the skin are important.

Therefore, there are known electrode arrangements with which the electrodes are attached to a belt-shaped electrode carrier consisting of an elastic material; to perform the measurement, the belt is wrapped around the patient's chest. The electrodes are attached to the patient's skin mechanically or with adhesive on the electrodes.

However, one disadvantage of this known electrode arrangement is that the individual electrodes cannot be positioned freely in the circumferential direction because it is difficult to adjust the positions of the individual electrodes due to the elasticity of the belt-shaped electrode carrier and the cross-sectional shape of the chest and it is difficult for the person performing the test to move them. In particular, with the known electrode arrangement it is impossible to adjust constant distances or angular distances between the individual electrodes, although that is important in electroimpedance tomography.

SUMMARY OF THE INVENTION

The object of the present invention is thus to improve upon the known electrode arrangement described above with a belt-shaped electrode carrier such that the individual electrodes can be attached to the patient's chest in the desired position.

Based on the known electrode arrangement described above according to the preamble of claim 1, this object is achieved through the characterizing features of claim 1, and with regard to a corresponding method for applying such an electrode arrangement, this object is achieved through the features of claim 25.

This invention includes the general technical teaching that the electrodes can be positioned on the belt-shaped electrode carrier in the longitudinal direction and/or in the circumferential direction of the belt-shaped electrode carrier, with the positioning preferably being free and constant within specified limits.

The positionability of the electrodes is preferably achieved in that the belt-shaped electrode carrier consists at least partially of a plastically deformable material. The positions of the individual electrodes on the chest are preferably distributed uniformly, preferably with constant angular distances, and/or can be modified by the person performing the test by stretching the belt-shaped electrode carrier between the individual electrodes until achieving the desired electrode spacing. Because of the plasticity of the material of the belt-shaped electrode carrier, this electrode distance is maintained even when the person performing the test is no longer exerting any force on the electrode carrier, which is the case, for example, when the electrode arrangement according to this invention is attached to a patient's chest.

The electrode carrier preferably stretches essentially uniformly over its length in the case of elongation in the longitudinal direction. In this way, uniform distances or angular distances between adjacent electrodes can be achieved to advantage, which is important for electroimpedance tomography. Therefore, the electrode carrier preferably consists of a material having a homogeneous expansion characteristic.

The plastically deformable material of the belt-shaped electrode carrier may be, for example, a plastic, but other materials are essentially also possible. It is not necessary for the belt-shaped electrode carrier to be made completely of a plastically deformable material. Instead it is sufficient if expansion sections made of a plastically deformable material are provided between the individual electrodes to permit positioning of the electrodes according to the desired positions of the electrodes on the patient's chest.

The free positionability of the electrodes in the longitudinal direction of the electrode carrier can also be achieved by folding the electrode carrier over itself in several layers between the electrodes. The distance between the electrodes can then be increased by pulling the electrode carriers apart in the longitudinal direction, so that the electrode carrier is partially unfolded.

A protective element is preferably arranged in the fold edges between the individual layers of the electrode carrier to prevent any interfering kinks from developing. This is advantageous because sharp kinks interfere with the free unfolding of the electrode carrier and thus would interfere with the positionability of the electrodes. The protective element preferably has a round cross section and has an outside diameter greater than the thickness of the electrode carrier. The protective element may be made of a plastic, for example, such as polyethylene (PE), but other materials are also possible.

To prevent unintentional automatic unfolding of the electrode carrier, the layers of the electrode carrier folded one over the other are preferably covered on both sides with an adhesive tape which secures the individual layers in the respective position if the electrode carrier is not pulled apart in the longitudinal direction. The individual layers of the electrode carrier thus form a package which is held together by the adhesive tape and is prevented from spontaneously unfolding.

In a preferred embodiment of the inventive electrode arrangement, connecting lines are provided for electric contacting of the electrodes, with the connecting lines being attached to the belt-shaped electrode carrier and being stretchable in the longitudinal direction of the belt-shaped electrode carrier so that damage to the connecting line with expansion of the belt-shaped electrode carrier in the circumferential direction is prevented.

One possibility for achieving stretchability of the connecting lines is to install the connecting lines in a meandering pattern so that expanding the belt-shaped electrode carrier in the longitudinal direction and or the circumferential direction leads to only a minor deformation of the connecting lines, so that damage to the connecting lines in expansion of the belt-shaped electrode carrier is prevented.

However, another possibility is for the connecting lines to consist of an electrically conductive and nevertheless mechanically extensible material so that a meandering layout of the connecting lines on the belt-shaped electrode carrier is unnecessary.

In one variant of this invention, the electrode carrier has a film on which the connecting lines and/or the electrodes are printed; this permits inexpensive mass production to advantage. The film preferably serves as a mechanical carrier and may be made of Mylar, for example.

The film preferably has an insulating layer on the side facing away from the measurement object in order to electrically insulate the connecting lines from the environment.

In addition, a shielding layer may also be provided, preferably applied to the insulation layer on the side facing away from the measurement object. Such a shielding layer consists of an electrically conducting material and is preferably applied to ground potential to shield the connecting lines of the electrodes from interfering electromagnetic fields.

The shielding may be designed to cover the entire area or each individual electrode and may be designed to be identical or slightly wider on the opposite side of the electrode carrier. The shielding may be grounded jointly or each individual electrode may be actively driven to common-mode rejection with the respective individual signal.

The electric contacting of the electrode paths and shielding paths on the plug is preferably accomplished by a double-sided plug connector. This double-sided connector can be plugged in through a reinforcement on the electrode carrier and contacted in a secured manner, e.g., by a pressure connection.

The belt-shaped electrode carrier preferably consists of several parts which are adjacent to one another in the longitudinal direction of the electrode carrier in the mounted state on the measurement object and can be joined together in pairs mechanically and/or electrically. Due to this division of the belt-shaped electrode carrier into several parts, mounting of the inventive electrode arrangement is facilitated, in particular in the case of bedridden patients on whom only a portion of the chest area is freely accessible.

The mechanical connection of the adjacent parts of the belt-shaped electrode carrier may be accomplished, for example, by a plug connection or by a crimp connection.

The individual parts of the belt-shaped electrode carrier are preferably attached to the measurement object separately from one another by gluing the parts, for example.

Furthermore, in an advantageous variant of this invention, a contact fluid is provided for electric contacting of the measurement object by the electrodes; this contact fluid is kept in a storage container, which is mounted on the belt-shaped electrode carrier. An optical and/or acoustic filling level indicator is preferably provided for the storage container, to notify the patient or the person performing the test promptly if the contact fluid has been consumed. The filling level indicator preferably generates an optical and/or an acoustic warning signal which gives an idea of the filling level in the storage container. The filling level indicator may be implemented by electrical or chemical means, but this invention can also be implemented with other physical mechanisms for determining the filling level in the storage container.

As one variant, the conductive electrode surface is provided with the thinnest possible layer of gel to minimize the contact resistance with the skin (impedance).

The electrode surface may be porous and the conductivity may be maintained by a reservoir of liquid and/or gel applied to the side of the electrode surface facing away from the body. This reservoir continuously supplied conductive fluid through the porous electrode surface into the contacting gel layer facing the patient's body.

In addition, this invention includes a method for applying the electrode arrangement described above to a measurement object such as the chest of a bedridden patient. In this case, first the electrodes are positioned in specified positions in the longitudinal direction of the belt-shaped electrode carrier, whereupon the electrode carrier is then applied with the electrodes to the measurement object, whereupon the electrodes establish electric contact with the measurement object.

The positioning of the electrodes in the longitudinal direction of the belt-shaped electrode carrier before applying the inventive electrode arrangement to the measurement object may be accomplished by stretching the belt-shaped electrode carrier in the longitudinal direction and/or circumferential direction between the electrodes, whereupon the resulting distance or angular distance, preferably a uniform distance which is thus set between the adjacent electrodes is subsequently maintained because of the plasticity of the material of the electrode carrier.

In an advantageous variant of this invention, a stencil is additionally used and is applied to the measurement object. For example, the stencil may be in the form of a strip placed around the patient's chest, with the excess length of the stencil being cut off, so that the length of the stencil is equal to the circumference of the patient's chest. Then the stencil may be folded repeatedly, resulting in equidistant folds along the stencil, forming markings for the positioning of the individual electrodes.

Then the stencil can be removed from the patient's chest and applied to the belt-shaped electrode carrier, and the electrode carrier can be stretched so that the positions of the individual electrodes match the positions of the folds.

In the multipart embodiment of the belt-shaped electrode carrier described above, it is especially simple to attach the inventive electrode arrangement, in particular in the case of a bedridden patient. To do so, first at least part of the belt-shaped electrode carrier is attached to the exposed area of the chest of the patient lying in bed. Then the patient is turned over, rotating about his longitudinal axis, whereupon then at least one other part of the belt-shaped electrode carrier is attached to the area of the patient's chest which is then exposed. Next, the individual parts of the belt-shaped electrode carrier can be joined together in pairs electrically and/or mechanically. However, the individual parts of the belt-shaped electrode carrier are preferably attached to the measurement object independently of one another and are connected electrically independently from one another.

The inventive electrode arrangement may essentially have any desired number of electrodes. However, the number of electrodes preferably amounts to a multiple of two or a power of two.

DESCRIPTION OF THE DRAWINGS

Other advantageous embodiment of this invention are characterized in the subclaims or are explained in greater detail below together with the description of the preferred exemplary embodiment according to this invention with reference to the figures, which show:

DETAILED DESCRIPTION OF THE PREFERRED EMBODIMENTS

Figure 1:
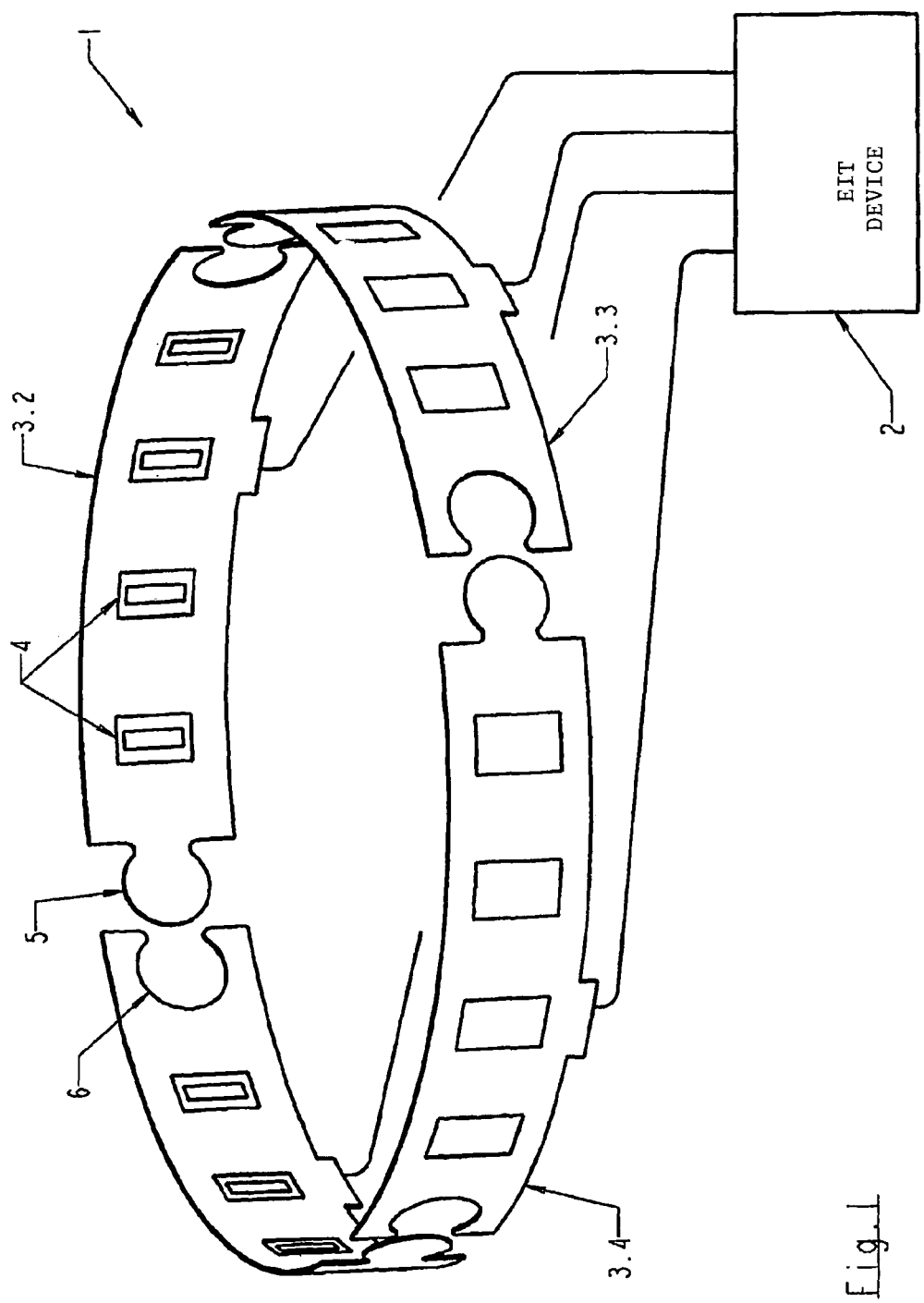
FIG. 1 an inventive electrode arrangement with a multipart belt-shaped electrode carrier and FIG. 2a an enlarged sectional view from the side of a part of the inventive electrode arrangement from FIG. 1, FIG. 2b a sectional view from the side of a part of the inventive electrode arrangement in normal size, FIG. 2c a view of a part of the inventive electrode arrangement, FIG. 3 a cross-sectional view of a part of another exemplary embodiment of an inventive electrode arrangement and FIG. 4 a cross-sectional view of a detail from FIG. 3.

The schematic diagram in FIG. 1 illustrates an inventive electrode arrangement 1, which may be connected to a traditional EIT device 2 for performing electroimpedance tomography.

The electrode arrangement 1 has a belt-shaped electrode carrier which in this exemplary embodiment consists of four parts 3.1-3.4, where the individual parts 3.1-3.4 of the electrode carrier each have four electrodes on their side facing the measurement object, these electrodes electrically contacting the patient's chest during the EIT measurement.

The individual electrodes 4 are rectangular and are aligned at a right angle to the longitudinal axis and/or to the circumferential direction of the belt-shaped longitudinal electrode carrier.

The individual parts 3.1-3.4 of the belt-shaped electrode carrier each consist of a plastically deformable plastic, which permits positioning of the electrodes 4 in the circumferential direction in order to be able to maintain specified electrode positions on the patient's chest during the measurement.

To do so, before the measurement a stencil in the form of a strip is placed around the patient's chest and the excess length of the stencil is cut off so that the length of the stencil corresponds to the circumference of the patient's chest. Then the stencil is folded four times along its longitudinal direction so that 15 equidistant folds are formed, each forming a mark for positioning the electrodes 4. The strip-shaped stencil is placed next to the electrode carrier with the individual parts 3.1-3.4 of the electrode carrier being stretched out so that one of the electrodes is at one end of the stencil while the positions of the other electrodes match the folds in the stencil.

In testing a bedridden patient by the EIT method, then part 3.1 of the belt-shaped electrode carrier is first placed on the exposed area of the patient's chest.

Then the patient is rotated about his longitudinal axis so that the second part 3.2 of the belt-shaped electrode carrier can then be applied to the area of the patient's chest which is then exposed.

Next the two parts 3.1 and 3.2 are separately connected electrically to the EIT device 2. This is done by using connecting lines, each of which has a color-coded plug to prevent a mix-up. The part 3.1 may have a connecting line with a blue plug, for example, while the plug on the connecting line for part 3.2 is red. The plug for part 3.3 may then be green, for example, while the plug for part 3.4 is yellow.

However, the mechanical connection between the adjacent parts 3.1-3.4 of the belt-shaped electrode carrier is accomplished by connections consisting of tongue-shaped plugs 5 and corresponding receptacles 6.

This procedure is then repeated for parts 3.3 and 3.4 of the belt-shaped electrode carrier until finally all the parts 3.1-3.4 of the belt-shaped electrode carrier have been attached to the patient's chest, whereupon the EIT tomography can begin.

Figure 2:
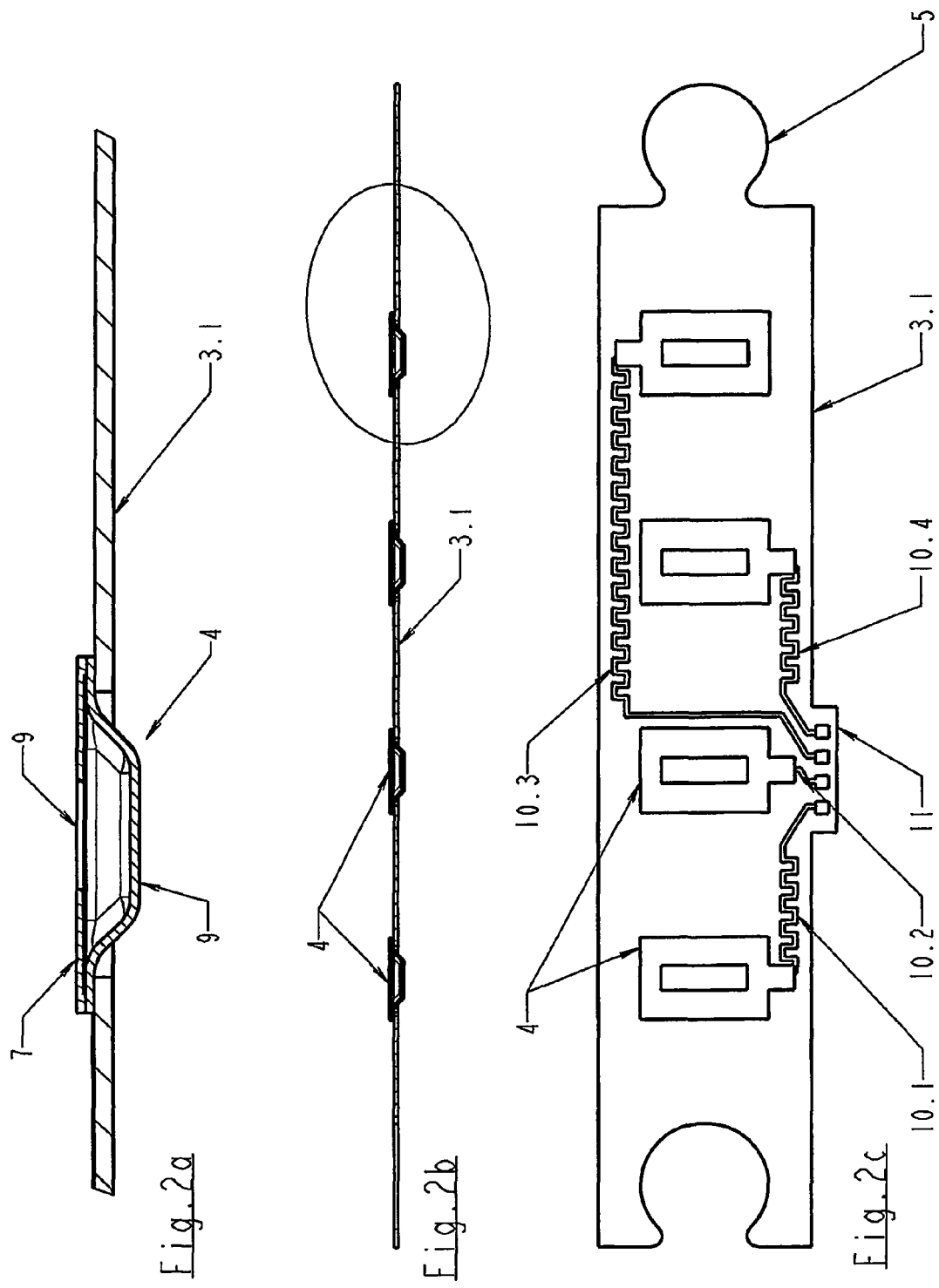

FIGS. 2a and 2b show side sectional views of one of the parts 3.1-3.4 of the inventive electrode arrangement, whereby FIG. 2 also shows the design of the individual electrodes 4.

The part 3.1 of the belt-shaped electrode carrier thus has a rectangular cutout in the area of each electrode 4.

On the side facing away from the measurement object, the cutout is covered by a liquid impermeable layer 7 which is welded at its edges to the part 3.1.

On the side facing the measurement object, however, the cutout in part 3.1 of the belt-shaped electrode carrier is covered by a partially permeable membrane 8.

The layer 7 and the membrane 8 enclose a contact fluid 9 which wets the surface of the measurement object and thereby reduces the contact resistance between the electrodes 4 and the measurement object.

In addition, it should be pointed out that the layer 7 is light permeable so that the person performing the test can perform a simple visual inspection of the liquid level in the electrodes 4 so that the electrode arrangement can be changed in due time.

FIG. 2c also shows that the individual electrodes 4 each have separate connecting lines 10.1-10.4 which are combined at a connection point 11, which permits contacting of all the electrodes 4 of part 3.1 by a single plug connection.

In addition, the connecting lines 10.1, 10.3 and 10.4 are designed to be meandering in the area between the individual electrodes 4. This guidance of the connecting lines 10.1, 10.3 and 10.4 offers the advantage that the connecting lines 10.1, 10.3, 10.4 are deformed only slightly with expansion of the part 3.1 in the longitudinal direction and/or the circumferential direction, which counteracts damage.

Figure 3:
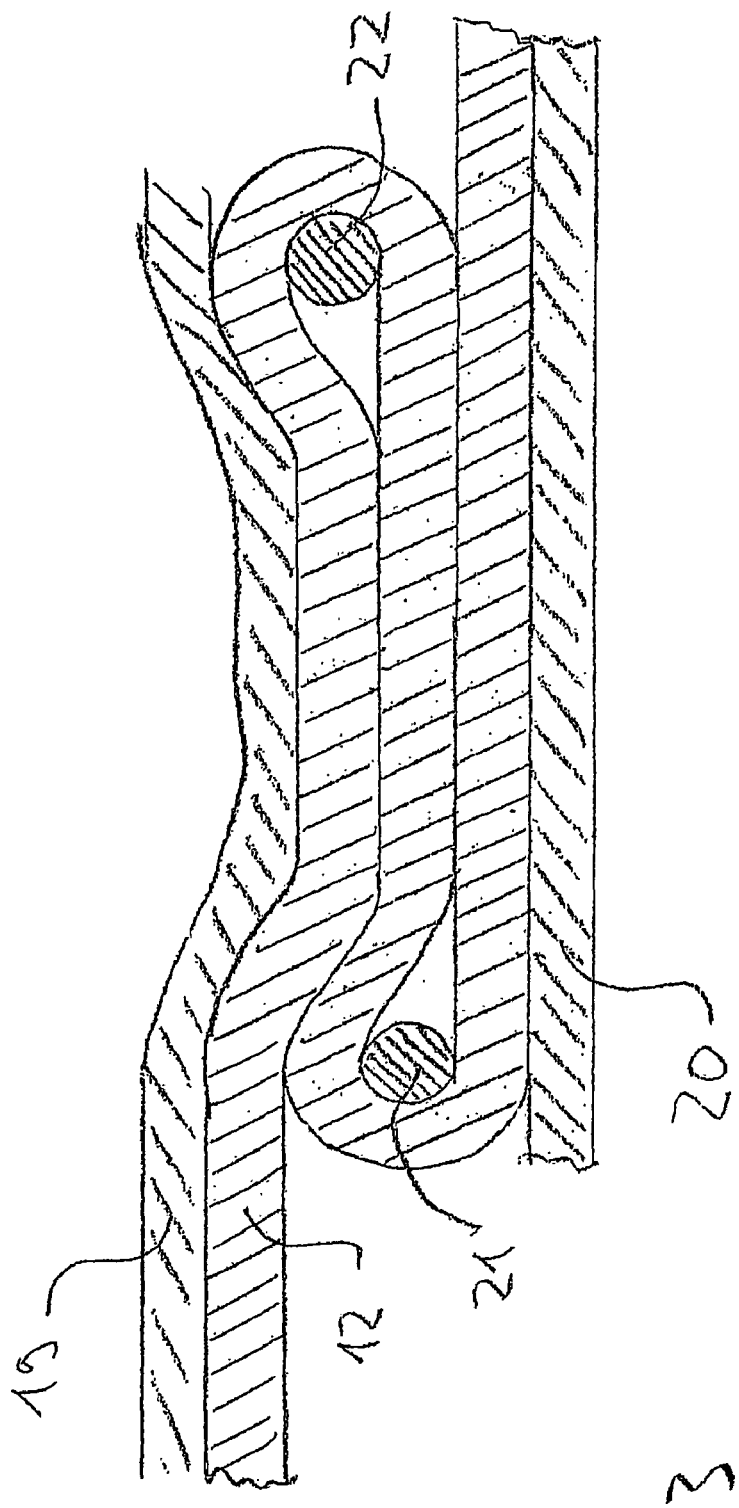

Finally, FIGS. 3 and 4 show a cross-sectional view of an electrode carrier 12 in which the extensibility in the longitudinal direction is achieved in a particular manner.

The electrode carrier 12 as a mechanical carrier element has a carrier film 13 which is made of Mylar and is covered on the side facing the measurement object with an adhesive layer 14 in order to be able to attach the electrode carrier 12 to the measurement object.

In supplying the electrode carrier 12 at the manufacturer's end, the adhesive layer 14 is covered on the side facing the measurement object with a removable protective layer 15 which is pulled away by the test person to expose the adhesive layer 14 before attaching it to the measurement object.

On the side of the carrier film 13 facing the measurement object, electrodes for contacting the measurement object are arranged at predetermined intervals, but these electrodes have not been shown in FIGS. 3 and 4 for the sake of simplicity. A printed conductor layer 16 is printed on the side of the carrier film 13 facing away from the measurement object in order to be able to electrically contact the electrodes by a separate connecting line for each.

The printed conductor layer 16 is in turn covered with an electric insulation layer 17 on the side facing away from the measurement object, thus preventing shunt circuits of the connecting lines.

Finally, a shielding layer 18 which electrically shields the connecting lines of the electrodes and thereby suppresses electromagnetic interference and increases the measurement accuracy is applied on the side of the insulation layer 17 facing away from the measurement object. The shielding layer 18 may be made of a vapor deposited metal layer, for example, and is preferably guided to an electric terminal with the connecting lines for the electrodes and is connected to ground potential there in order to achieve a good shielding effect.

The shielding may be provided over the entire area or for each individual electrode and may be designed to be identical or slightly wider on the opposite side of the electrode carrier. The shielding may be jointly grounded as well as actively driven for each individual electrode with the respective individual signal for common mode rejection.

The electric contacting of the electrode paths and the shielding paths on the plug is preferably accomplished by a double-sided plug connector. This double-sided plug may be connected to the electrode carrier through a reinforcement and contacted in a secured manner by a pressure connection, for example.

Between neighboring electrodes in the longitudinal direction, the electrode carrier 12 is folded in several layers one above the other as illustrated in FIG. 3. This permits an expansion of the electrode carrier 12 in the longitudinal direction in that the electrode carrier 12 is pulled apart in the longitudinal direction by the person performing the test, whereupon the electrode carrier 12 is unfolded.

To prevent an unwanted automatic unfolding of the electrode carrier 12, the layers of the electrode carrier 12 arranged one above the other are covered on both sides with an adhesive tape 19, 20 which secures the individual folded layers in the respective position as long as the person performing the test does not pull the electrode carrier 12 in the longitudinal direction. The adhesive tape 19, 20 thus ensures that the electrode carrier 12 will not unfold spontaneously during shipping and storage or during the actual testing, which would result in an unintentional and undefined change in the electrode positions.

Finally, a protective element 21, 22 is provided between the individual stacked and folded layers of the electrode carrier 12 in each of the fold edges to prevent kinks. This is advantageous because kinking would interfere with the unfolding of the electrode carrier 12 and thus would interfere with the free positioning of the electrodes. The protective elements 21, 22 each have a circular cross section and have an outside diameter which is slightly larger than the thickness of the electrode carrier 12.

This invention is not limited to the exemplary embodiment described above but instead a number of variants and modifications are possible, which also make use of the inventive idea and therefore fall within the scope of the present invention.

The invention claimed is:

1. An electrode arrangement for electroimpedance tomography, having
multiple electrodes for electric contacting of a measurement object, and
a belt-shaped electrode carrier for surrounding the measurement object,
whereby the electrodes are mounted on the belt-shaped electrode carrier,
wherein the electrodes are positioned on the belt-shaped electrode carrier in the longitudinal direction of the belt-shaped electrode carrier, wherein
the belt-shaped electrode carrier comprises several parts adjoining each other on the measurement object in the longitudinal direction of the electrode carrier in the mounted state and having connections joining together the several parts mechanically in pairs in the mounted state.

2. The electrode arrangement according to claim 1, wherein the electrodes are freely and permanently positioned on the belt-shaped electrode carrier in the longitudinal direction of the belt-shaped electrode carrier.

3. The electrode arrangement according to claim 1, wherein the belt-shaped electrode carrier-comprises at least in part a plastically deformable material to permit positionability of the electrodes.

4. The electrode arrangement according to claim 3, wherein the plastically deformable material is a plastic or a woven material with a plastic coating.

5. The electrode arrangement according to claim 1, wherein the electrode carrier is folded in several layers one above the other between two neighboring electrodes.

6. The electrode arrangement according to claim 5, wherein at least one protective element for preventing kinks from developing is arranged between the individual layers of the electrode carrier in at least one fold of the electrode carrier.

7. The electrode arrangement according to claim 5, wherein the layers of the electrode carrier folded one above the other are attached by at least one adhesive element to prevent them from spontaneously unfolding.

8. The electrode arrangement according to claim 7, wherein the layers of the electrode carrier folded one above the other are covered with an adhesive tape on both sides to prevent them from spontaneously unfolding.

9. The electrode arrangement according to claim 1, wherein the electrode carrier expands essentially uniformly over its length when stretched in the longitudinal direction.

10. The electrode arrangement according to claim 1, wherein, connecting lines are provided for electric contacting of the electrodes whereby the connecting lines are attached to the belt-shaped electrode carrier and can be expanded in the longitudinal direction of the belt-shaped electrode carrier.

11. The electrode arrangement according to claim 10, wherein the connecting lines run in a meandering pattern on the belt-shaped electrode carrier.

12. The electrode arrangement according to claim 10, wherein the connecting lines are made of an electrically conductive and expandable material.

13. The electrode arrangement according to claim 10, wherein the electrode carrier is a film, with the electrodes and/or the connecting lines being applied to the film.

14. The electrode arrangement according to claim 1, wherein the electrode carrier is covered at least partially with an electric insulation layer on either a side adapted to be facing the measurement object or a side adapted to be facing away from the measurement object.

15. The electrode arrangement according to claim 1, wherein the electrode carrier is covered at least partially by an electric shield on either a side adapted to be facing the measurement object or a side adapted to be facing away from the measurement object.

16. The electrode arrangement according to claim 15, wherein the shield covers the entire surface or is limited to the area of the electrodes.

17. The electrode arrangement according to claim 15, wherein the shield is grounded or is acted upon by the respective individual signal for common-mode rejection.

18. The electrode arrangement according to claim 1, wherein a joint or a crimp connection is provided for mechanical connection of adjacent parts of the belt-shaped electrode carrier.

19. The electrode arrangement according to claim 1, wherein a contact fluid which is stored in a storage container is provided for electric contacting of the measurement object, whereby the storage container is accommodated on the belt-shaped electrode carrier.

20. The electrode arrangement according to claim 19, wherein the storage container is integrated into the electrodes.

21. The electrode arrangement according to claim 1, wherein the electrodes are at least partially covered with a gel layer.

22. A method for applying an electrode arrangement according to claim 1 to a measurement object comprising the following steps:
positioning the electrodes in the longitudinal direction of the belt-shaped electrode carrier at predetermined positions; and
attaching the electrode carrier to the measurement object, whereby the electrodes contact the measurement object.

23. The method according to claim 22, wherein the belt-shaped electrode carrier is stretched between the electrodes for positioning the electrodes in the longitudinal direction of the electrode carrier.

24. The method according to claim 23, further comprising the following steps:
- wrapping a stencil around the measurement object,
- shortening the stencil to the circumference of the measurement object,
- creating equidistant markings on the stencil,
- applying the stencil to the belt-shaped electrode carrier, and
- equidistant positioning of the electrodes by expansion on the belt-shaped electrode carrier corresponding to the marks on the stencil.

25. The method according to claim 24, wherein the stencil is removed from the measurement object before being applied to the electrode carrier.

26. The method according to claim 22, wherein the measurement object is a person's body part, whereby the following steps are to be carried out:
- attaching at least one part of the belt-shaped electrode carrier to an exposed part of the patient's body part,
- rotating the body part,
- attaching at least one additional part of the belt-shaped electrode carrier to the exposed part of the patient's body part, and
- connecting the parts of the belt-shaped electrode carrier together in pairs.

27. The method according to claim 26, wherein the body part is the chest, neck or head.

* * * * *